US008334970B2

(12) United States Patent
Wildenbeest et al.

(10) Patent No.: US 8,334,970 B2
(45) Date of Patent: Dec. 18, 2012

(54) DETECTION OF OPEN CRACKS IN EGGS

(75) Inventors: Erik Jan Wildenbeest, De Heurne (NL);
Dirk Willem Wikkerink, Aalien (NL);
Jan Willem Pennings, Gendringen (NL)

(73) Assignee: Staalkat International B.V., Aalten (NL)

( * ) Notice: Subject to any disclaimer, the term of this patent is extended or adjusted under 35 U.S.C. 154(b) by 573 days.

(21) Appl. No.: 12/300,879

(22) PCT Filed: Mar. 1, 2007

(86) PCT No.: PCT/NL2007/000054
§ 371 (c)(1),
(2), (4) Date: Apr. 7, 2009

(87) PCT Pub. No.: WO2007/133063
PCT Pub. Date: Nov. 22, 2007

(65) Prior Publication Data
US 2010/0026989 A1    Feb. 4, 2010

(30) Foreign Application Priority Data
May 16, 2006   (NL) ...................................... 1031823

(51) Int. Cl.
*A01K 43/00*    (2006.01)
*G01N 33/08*    (2006.01)
(52) U.S. Cl. ....................................................... 356/57
(58) Field of Classification Search .................. 382/110;
356/56–58, 61, 63–66
See application file for complete search history.

(56) References Cited

U.S. PATENT DOCUMENTS 1,796,699 A *  3/1931  Wyland .......................... 356/57
3,067,605 A * 12/1962  Bliss ............................ 73/12.09
(Continued)

FOREIGN PATENT DOCUMENTS
DE         1581043 A1    5/1971
(Continued)

*Primary Examiner* — Tarifur Chowdhury
*Assistant Examiner* — Michael P Lapage
(74) *Attorney, Agent, or Firm* — Kilpatrick Townsend & Stockton LLP

(57) ABSTRACT

A conveying device for conveying eggs comprises an endless conveyor provided with rollers extending transversely to the direction of conveyance. The rollers are arranged in pairs, and each pair of rollers forms an receiving space, in which an egg is accommodated in such a way that the egg rests on both rollers. The conveying device furthermore comprises a transfer device provided with a plurality of pick-up elements for picking up the eggs from a tray and placing the eggs on the conveyor. The pick-up elements on the transfer device can be moved from a first position in which they are positioned at a distance from each other corresponding to the distance between the individual eggs on the tray, viewed in the direction of conveyance, and a second position corresponding to the centre-to-centre distance between two receiving spaces. In use, the rollers are set in rotation, with the result that an egg resting on them is set in rotation, which is advantageous if the eggs on the conveyor have to be inspected for cracks. In this case by means of a plurality of lasers disposed in a stationary position one after the other a laser beam is directed at the egg during movement of the egg, and the light transmission of the egg surface is observed by optical observation means. Data processing means are equipped to decide on the basis of the observed light transmission whether or not an egg has a crack.

18 Claims, 9 Drawing Sheets

U.S. PATENT DOCUMENTS

| | | | |
|---|---|---|---|
| 3,091,323 A | | 5/1963 | Niederer, Jr. et al. |
| 3,298,499 A | | 1/1967 | Ellis et al. |
| 3,342,012 A | * | 9/1967 | Reading .................. 53/494 |
| 3,929,234 A | * | 12/1975 | Warren .................. 414/737 |
| 4,161,366 A | * | 7/1979 | Bol et al. .................. 356/56 |
| 4,872,564 A | * | 10/1989 | van der Schoot ............. 209/511 |
| 5,030,001 A | * | 7/1991 | vande Vis .................. 356/53 |
| 5,615,777 A | * | 4/1997 | Weichman et al. ............ 209/511 |
| 5,900,929 A | * | 5/1999 | Hebrank et al. ................ 356/52 |
| 6,373,560 B1 | * | 4/2002 | Roux .......................... 356/58 |
| 2003/0227613 A1 | | 12/2003 | Hebrank |
| 2006/0165830 A1 | * | 7/2006 | Korndorfer et al. ....... 425/126.2 |

FOREIGN PATENT DOCUMENTS

| | | |
|---|---|---|
| FR | 1305325 A | 10/1962 |
| GB | 356734 A | 9/1931 |
| JP | 53-136777 U | 10/1978 |
| JP | 07-209209 A | 8/1995 |
| JP | 09-243555 A | 9/1997 |
| JP | 11-314611 A | 11/1999 |
| JP | 2001-037367 A | 2/2001 |
| JP | 2003-081223 A | 3/2003 |
| NL | 6813606 A | 3/1970 |
| NL | 7701472 A | 8/1977 |
| NL | 8204580 A | 6/1984 |
| WO | WO 96/22528 A | 7/1996 |

* cited by examiner

DETECTION OF OPEN CRACKS IN EGGS

CROSS-REFERENCE TO RELATED APPLICATIONS

This application is a National Stage of International Application No. PCT/NL2007/000054, filed Mar. 1, 2007, and which claims the benefit of Neatherlands Patent Application No. 1031823, filed May 16, 2006, the disclosures of both applications being incorporated herein by reference.

BACKGROUND OF THE INVENTION

The invention relates to the detection of eggs with an open crack. During the grading of eggs, leaking eggs, the so-called open-crack eggs, cause soiling of the machine and soiling of other eggs. These open-crack eggs therefore need to be detected at as early a stage as possible without other eggs being soiled. A system for detecting and removing leaking eggs therefore has two related aspects: to prevent soiling before the detection and remove broken eggs, and to detect the broken eggs themselves.

In the case of a known device, eggs are picked up from a cardboard tray by the transfer device and then placed on a conveyor of a machine, for example a grading machine. The device has several pick-up elements, for example suction cups, which are each connected by way of a corresponding channel to a common pressure space in which a vacuum can be applied by means of a vacuum pump. The transfer device picks up a plurality of rows of eggs from the tray in one go by means of the suction cups and then places said eggs on the conveyor of the conveying device. The receiving spaces of the conveyor in the known conveying device are formed by two successive rollers, each roller bounding two receiving spaces. The centre-to-centre distance between the receiving spaces in the direction of conveyance corresponds approximately to the centre-to-centre distance between the eggs on the tray. Since two eggs generally rest on each roller, there is a risk that if an egg is split or cracked, the contents of the egg is transferred by means of the rotating roller from one egg to the other egg. The result of this smearing of the contents of the broken egg is that the conveyor and the eggs on it quickly become soiled, which is undesirable.

The object of the invention is to provide an improved conveying device in which the problem of smearing is overcome.

SUMMARY OF THE INVENTION

This object is achieved according to a first aspect of the invention by a conveying device for conveying eggs, comprising an endless conveyor provided with rollers extending transversely to the direction of conveyance. The rollers are placed at such a centre-to-centre distance from each other that they form between them a receiving space, in which in use an egg is received in such a way that the egg rests on both rollers. The rollers are rotatably mounted and can be driven so that in use they set an egg resting on them in rotation. and the conveying device furthermore comprises a transfer device provided with a plurality of pick-up elements for picking up the eggs from a tray and placing the eggs on the conveyor. The rollers are arranged in pairs and each receiving space is formed by a pair of rollers. The pick-up elements on the transfer device can be moved from a first position in which they are positioned at a distance from each other corresponding to the distance between the individual eggs on the tray, viewed in the direction of conveyance, and a second position corresponding to the centre-to-centre distance between two receiving spaces on the conveyor, viewed in the direction of conveyance.

Owing to the fact that according to the invention successive receiving spaces are defined as a receiving space formed by a pair of successive rollers, in the case of which each roller—unlike the conveying device known from the prior art—belongs to only one pair of rollers, only one egg generally rests on each roller and the smearing effect is prevented. The construction does mean that the centre-to-centre distance between the receiving spaces is greater than that of the conveying device known from the prior art. This means that the centre-to-centre distance between the eggs on the tray and the centre-to-centre distance between the receiving spaces no longer correspond. By means of the transfer device in the conveying device according to the invention the eggs are moved apart after being picked up from the tray, until they are at a distance from each other that corresponds to the mutual positions of the receiving spaces of the conveyor. The eggs are then deposited by the transfer device on the moving conveyor in the defined receiving spaces.

Since according to the invention the receiving spaces for the eggs on the conveyor are at a greater distance from each other, it is desirable to make the conveyor run faster in order to achieve the same conveyance capacity. The conveyor used is preferably the same conveyor as that used in the abovementioned conveyor according to the prior art, which is already available. In this case eggs are then always placed in a row of receiving spaces, and the following row of receiving spaces present per se in the conveyor is left empty. In order to achieve the same capacity, this conveyor would have to move twice as fast as it would if all rows were filled. A problem which can occur with this solution is that the transfer device does not place eggs exactly in the middle (in the direction of conveyance) of the receiving spaces. Since the eggs are deposited in an upright position, it can happen that they topple over the roller and end up in the wrong position in receiving spaces which had to be left open in order to avoid smearing. For that reason, according to a preferred embodiment of the invention, blocking elements are provided, each positioned or capable of being positioned in a space between two pairs of rollers, in order to block incorrect positioning of eggs in that space. This solution works not only in the case of known conveyors as mentioned, but also in the case of conveyors in which the pairs of rollers have been placed closer together.

Another aspect of the invention relates to the inspection of eggs for cracks. In particular this aspect relates to an inspection device for inspecting eggs for cracks, comprising a laser for exposing the egg to a laser beam, optical observation means for observing the light transmission by the egg, data processing means that on the basis of the light transmission observed by the observation means are adapted to emit a decision signal that is representative for the decision of whether or not an egg has a crack, and also a conveying device for conveying the eggs past the laser and observation means, which conveying device is furthermore adapted to rotate the eggs during the conveyance.

NL 7701472 in the name of the applicant discloses a device in which the egg is rotated on the conveyor by means of the rollers. Furthermore, by means of annular mirrors and a rotating prism, a laser beam is rotated around the egg about an axis that is perpendicular to the direction of rotation of the egg. In this way the surface of the egg is fully scanned by a laser beam. The known device also has a light detector. Part of the laser light penetrates through the eggshell and is uniformly distributed inside the egg, with the result that the egg gives out light. Part of this light goes into the light detector. When the laser beam reaches a crack, a greater part of the laser light passes through the shell into the egg because of the crack. As a result of this, the light detector will detect a greater light intensity of the light scattered from the egg, and on that basis it can be established that the egg contains a crack.

The aim is to provide an improved inspection device of the type described above.

This aim is achieved according to the present aspect of the invention by an inspection device for inspecting eggs for cracks, comprising a laser for exposing the egg to a laser beam, optical observation means for observing the light transmission by the egg, data processing means that on the basis of the light transmission observed by the observation means are adapted to emit a decision signal that is representative for the decision of whether or not an egg has a crack, and also a conveying device for conveying the eggs past the laser and observation means, which conveying device is furthermore adapted to rotate the eggs during the conveyance. The inspection device is characterized in that the device comprises a plurality of lasers disposed in a stationary position one after the other in the direction of conveyance, for the purpose of exposing one egg after the other to a stationary laser beam during the movement of the egg by means of the conveying device.

With this solution according to the invention the laser beam is directed at an arbitrary point of the egg. The surface of the egg is not therefore scanned, as is the case in the prior art. The observation means, preferably comprising at least one camera, observe the entire surface of the egg because of the fact that the egg rolls over during the conveyance past the lasers. Laser light entering the egg through the eggshell is scattered in the egg and comes back out through the eggshell. If an egg has a crack, more light will come out at that point, and this is observed by the observation means. On that basis it can be established that the egg is cracked or broken. Instead of a camera, observation means with a plurality of photosensitive elements could also be used, by means of which elements the light intensity of the various parts of the surface of the egg can be compared with each other.

The lasers are turned on when an egg is in front of them, and are switched off again when it has passed. It is necessary to switch off the lasers in order to prevent the laser beam from falling through openings in the conveyor directly onto the observation means and blinding the latter.

The inspection device preferably comprises detection means for detecting whether an egg is present in the receiving space between two rollers, which detection means are connected to a control unit for the lasers, which control unit is equipped to switch on the lasers in succession, depending on the egg detection by the detection means, at the moment when the receiving space containing an egg is passing the particular laser, and to switch them off again when the receiving space has passed the laser concerned.

An inspection device according to the second aspect of the invention is advantageously provided with a conveying device according to the first aspect of the invention.

BRIEF DESCRIPTION OF THE DRAWINGS

The invention will be explained in greater detail with reference to the drawing, in which.

DETAILED DESCRIPTION

Figure 1:
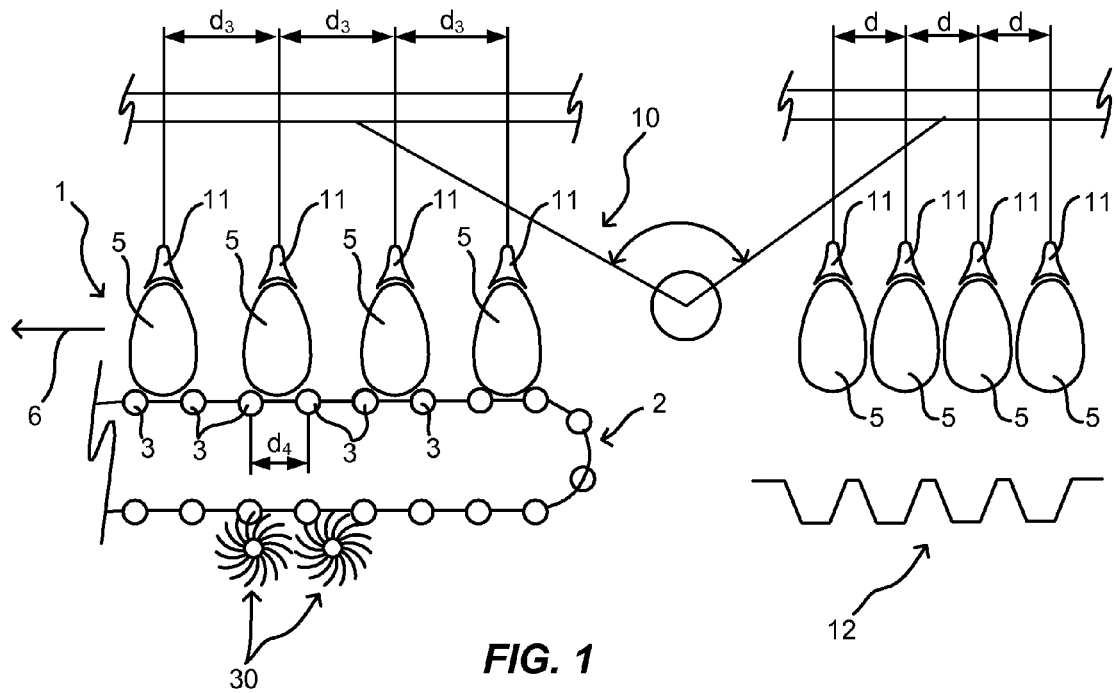
FIG. 1 shows a side view of a conveying device according to a first aspect of the invention.
Figure 2:
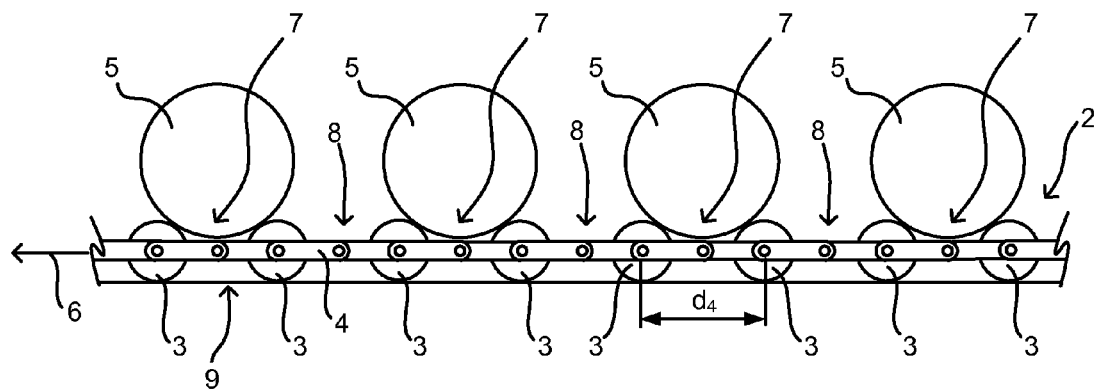
FIG. 2 shows a detail of the device shown in FIG. 1.

FIG. 1 shows diagrammatically a conveying device 1 for conveying eggs 5. The conveying device 1 comprises an endless conveyor 2 provided with rollers 3 extending transversely to the direction of conveyance. The rollers 3 are connected to each other by means of chains 4. The rollers 3 are preferably of identical shape and dimensions. The conveyor 2 in general has rows of a plurality of rollers 3, for example six or a multiple of six, placed widthwise next to each other. The rows of rollers 3 are connected to each other by means of chains. The rollers 3 are placed at a centre-to-centre distance $d_4$ in the direction of conveyance (indicated by arrow 6) which is such that they form between them a receiving space 7 in which in use an egg 5 is accommodated in such a way that the egg 5 rests upon both rollers 3, as can be seen clearly in FIG. 2. The rollers 3 are arranged in pairs and each receiving space 7 is formed by a pair of identical rollers 3. According to the invention, in order to prevent smearing, no egg is placed in the space 8 between two pairs of rollers, which space 8 in the case shown is of the same size as the receiving spaces 7. The rollers 3 are rotatably mounted and on the side facing away from the egg they act upon a supporting surface 9, so that through the movement of the conveyor 2 the rollers 3 are rotated and in use set an egg 5 resting on them in rotation by means of friction contact. The rollers 3 could also be set in rotation in another way.

One or more brushes 30 (see FIG. 1) are provided on the return side of the conveyor 2 in order to remove broken egg or other dirt from the rollers 3.

The conveying device 1 furthermore comprises a transfer device 10 provided with a plurality of pick-up elements in the form of suction cups 11 for picking up the eggs 5 from a tray 12 and placing the eggs 5 on the conveyor 2. At least in the area where the eggs are taken from the tray 12 and placed on the conveyor 2, the conveyor 2 extends substantially in the horizontal direction. The suction cups 11 are placed from the top against the eggs 5 on the tray 12 and from a vacuum space (not shown) a vacuum is then applied in the suction cups 11 relative to the environment, with the result that the eggs 5 are sucked against the suction cups 11. This provides sufficient retaining force to lift the eggs 5 from the tray 12 and move them to the conveyor 2. In order to release the eggs 5, the vacuum in the vacuum space is removed by, for example, admitting entrained air from the environment through a controllable valve (not shown).

The suction cups 11 have on the transfer device 10 a first position (shown on the right in FIG. 1), in which the suction cups 11 are positioned at a distance d from each other which corresponds to the distance, viewed in the direction of conveyance 6, between the eggs 5 on the tray 12. After picking up the eggs 5, the suction cups 11 on the transfer device 10 can be moved to a second position (shown on the left in FIG. 1), in which they are positioned at a distance $d_3$ from each other which corresponds to the centre-to-centre distance between two receiving spaces 7 on the conveyor 2. In the case shown the spaces 8 left empty between the pairs of rollers and the receiving spaces 7 of a pair of rollers are of the same size, so that the distance between the suction cups 11, viewed in the direction of conveyance 6, corresponds to twice the centre-to-centre distance $d_4$ between two rollers 3.

Because the eggs 5 are deposited in an upright position and are therefore not stable, it can happen that they topple over the roller 3 and land incorrectly in a space 8 which needed to be left open in order to prevent smearing. For that reason, it is preferable to provide blocking elements that are each positioned in a space between two pairs of rollers at the moment when the eggs 5 are being placed by the transfer device 10 on the conveyor 2, in order to block incorrect placing of eggs 5 in those spaces 8.

Figure 3:
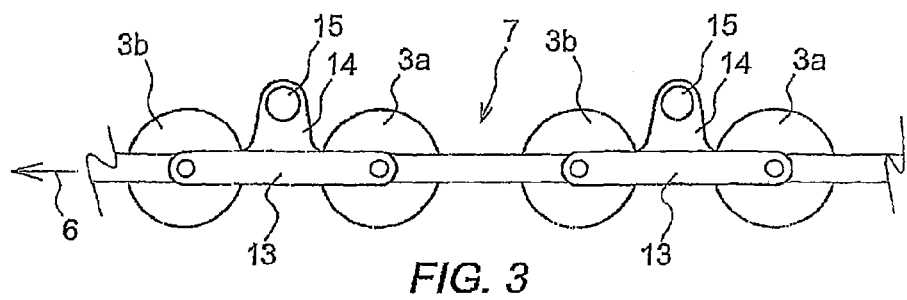
FIG. 3 shows a detail of a preferred embodiment of a conveying device according to the first aspect of the invention, provided with blocking means.

FIG. 3 shows how, viewed in the direction of conveyance 6, a rear roller 3b of a pair of rollers and a front roller 3a of a pair of rollers situated directly behind are connected to each other by means of a connecting element 13. An upwardly projecting member 14 is provided on the connecting element 13. A blocking bar 15 or the like can be fixed on the upwardly projecting member 14, which blocking bar or the like extends in the transverse direction of the conveyor 2 into the space between the rollers 3.

Figure 4:
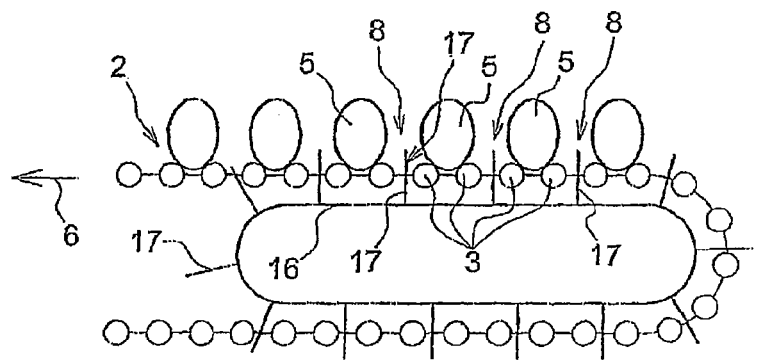
FIG. 4 shows a diagrammatic view of another preferred embodiment of a conveying device according to the first aspect of the invention, provided with blocking means.
Figure 5:
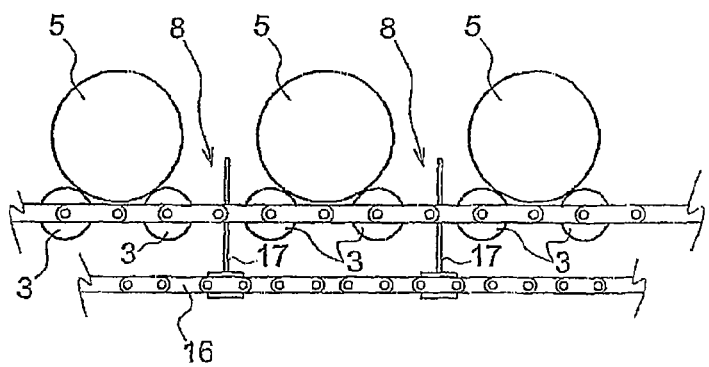
FIG. 5 shows a detail of the device of FIG. 4.

FIG. 4 and FIG. 5 illustrate another preferred embodiment in which blocking pins 17 or other blocking elements are provided on a conveyor chain 16 or another endless circulating element, which blocking elements extend substantially perpendicularly to the chain 16. The chain 16 extends in the direction of conveyance 6 of the conveyor 2 along a length at least corresponding to the number of eggs 5 to be placed by the transfer device 10 in one go one after the other on the conveyor 2. In operation, the chain 16 runs at the same speed as the conveyor 2. Owing to the fact that the chain 16 and the conveyor 2 run in synchronism, the blocking pins 17 in this embodiment can be inserted from the underside in each case into the space 8 between two pairs of rollers.

Figure 6:
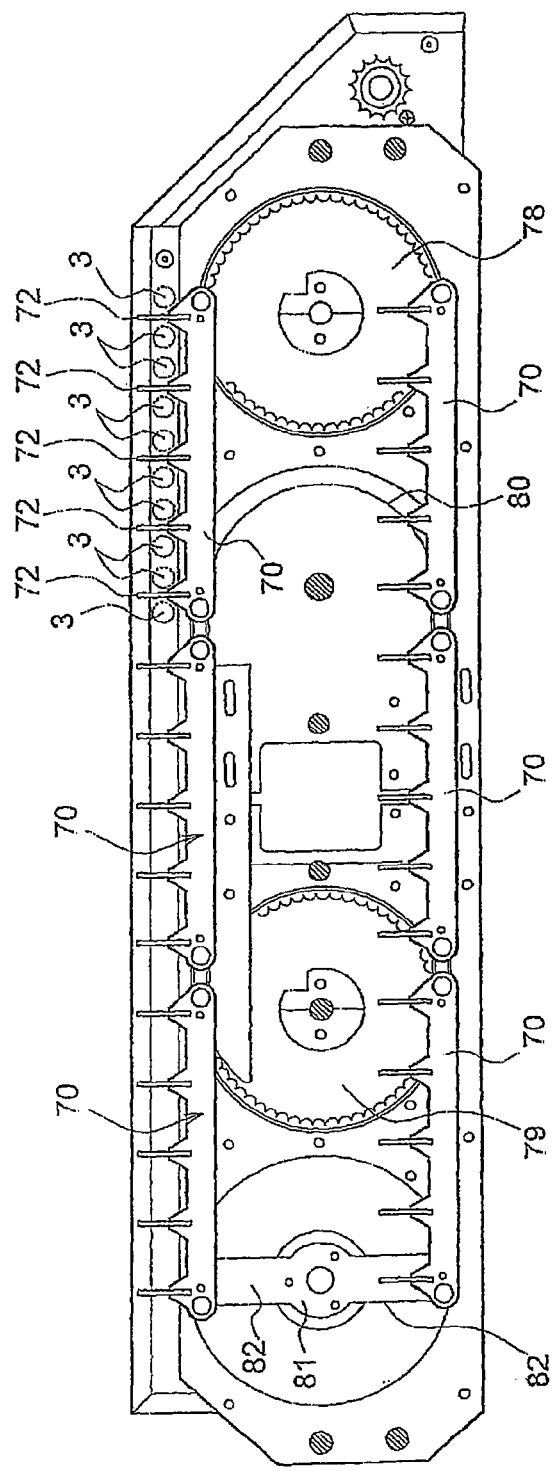
FIG. 6 shows a side view of a blocking unit with blocking means for a conveying device operating according to the principle of FIG. 4.
Figures 7, 8:
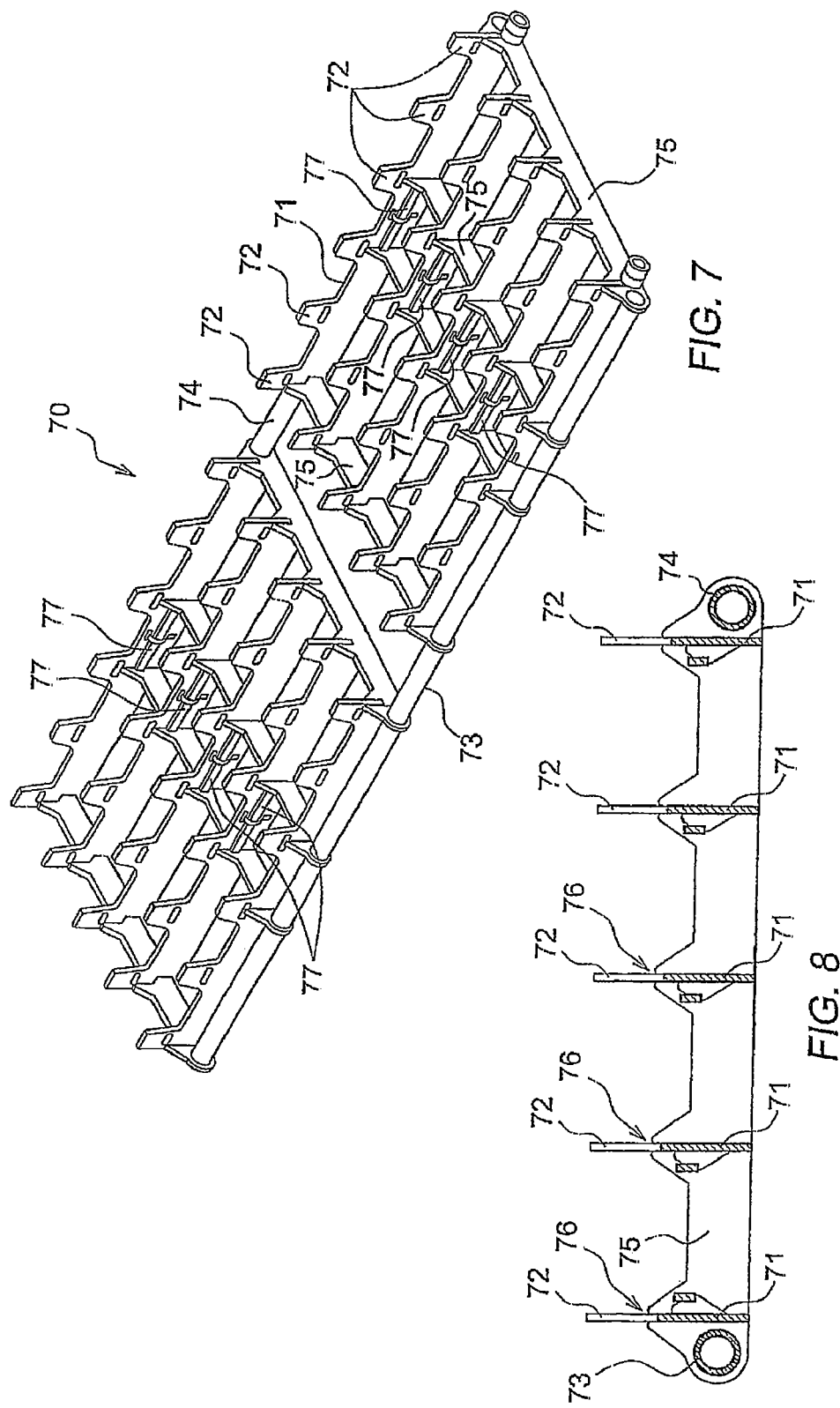
FIG. 7 shows a view in perspective of a frame provided with blocking lips for the blocking unit of FIG. 6.
FIG. 8 shows a side view of the frame of FIG. 7.

FIGS. 6-8 show a preferred embodiment of a blocking device in more detail. FIG. 7 shows a frame 70, in which five elongated plates 71 are fitted parallel to each other. The elongated plates 71 are provided with six blocking lips 72 on the upper side. In the embodiment shown two plates are always disposed next to each other widthwise, so that twelve blocking lips 72 are therefore placed next to each other for use with a conveyor 2 with twelve rows. The frame 70 has two cross-bars 73 and 74 respectively, which are connected by a plurality of longitudinal strips 75. The elongated plates 71 with the blocking lips 72 are pushed from the top into receiving slits 76 in the longitudinal strips 75 (see FIG. 8) and are retained in the slits 76 by means of a centrally disposed clamping system 77 provided with a spring or the like. The elongated plates 71 with the blocking lips 72 can be removed from the frame 70 for cleaning by releasing the clamping system 77.

FIG. 6 shows the blocking device with six frames 70, which are connected to each other by means of chains. The frames 70 are conveyed around in a so-called paternoster (continuously moving) system. During the circulation here the frames 70 remain horizontal, and the blocking lips 72 remain directed vertically upwards. Owing to the fact that the frames 70 are conveyed around by a paternoster system, the blocking lips 72 are inserted approximately straight from the bottom into the spaces 8 between the rollers 3, a plurality of which are indicated in dotted lines for purposes of illustration. During the movement upwards (on the right in FIG. 6) the frame 70 is driven by chain wheel 78 at one end, and the other end of the frame 70 is guided by a guide track 80. During the movement downwards each frame 70 is driven by a chain wheel 79 at one end, and by a rotating support element 81 with radially extending vanes 82 at the other end.

Figure 9:
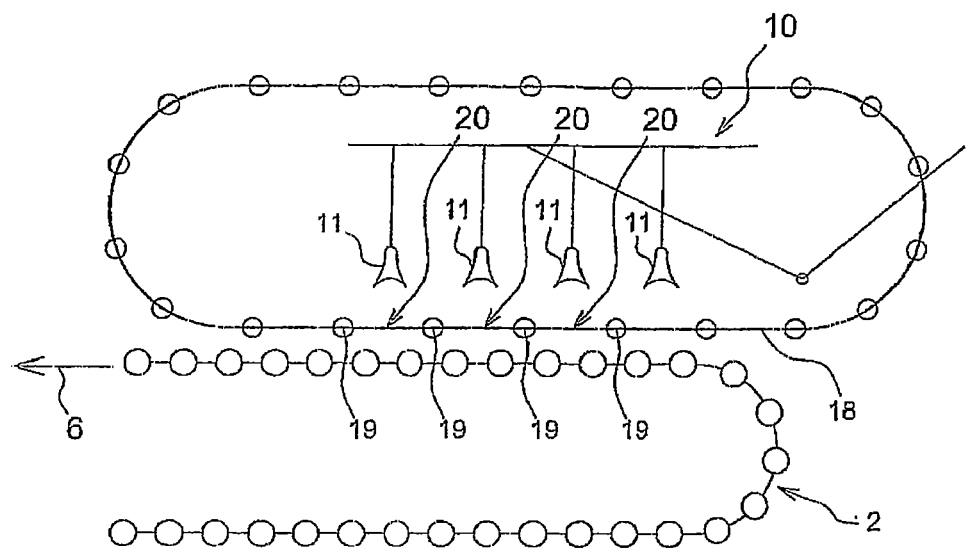
FIG. 9 shows yet another preferred embodiment of a conveying device according to the first aspect of the invention, provided with blocking means.
Figure 10:
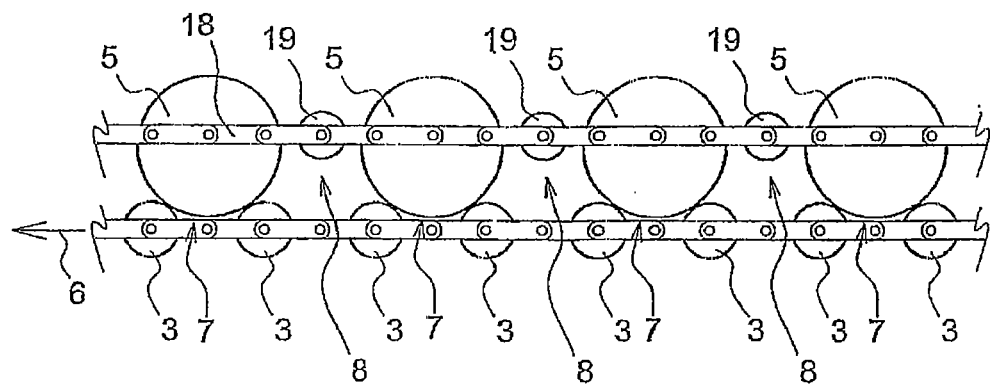
FIG. 10 shows a detail of the device of FIG. 9.

FIG. 9 and FIG. 10 show diagrammatically yet another preferred embodiment, in which a chain 18 or another endless circulating element with blocking bars 19 is fitted above the conveyor 2. The chain 18 extends in the direction of conveyance 6 of the conveyor 2 along a length corresponding at least to the number of eggs 5 to be placed by the transfer means 10 in one go one after the other on the conveyor 2. In operation, the chain 18 with the blocking bars 19 runs in synchronism with the conveyor 2. The blocking bars 19 run along with the chain above the spaces 8 between the pairs of rollers that have to remain empty, or are inserted into said spaces from the upper side of the conveyor 2 and, as it were, screen off said spaces 8. Passages 20 are provided between the parallel blocking bars 19 in order to allow through the suction cups 11 when the eggs 5 are being deposited in the receiving spaces 7.

FIG. 13 and FIG. 14 show diagrammatically an alternative embodiment, in which a photoelectric cell 130 or another suitable detection means is placed above the conveyor 2. The pairs of rollers 3 with their receiving spaces 7 and the spaces 8 lying between the pairs of rollers pass the photoelectric cell 130, which detects whether an egg 5 is present in a receiving space 7, or if an egg 5 is present in a space 8 in front of or behind that space. The photoelectric cell 130 is preferably connected by means of a control unit 131 to a movement means in order to move an incorrectly placed egg 5, depending on the situation, from a space 8 between two pairs of rollers forwards or backwards to the correct receiving space 7.

Figure 13A:
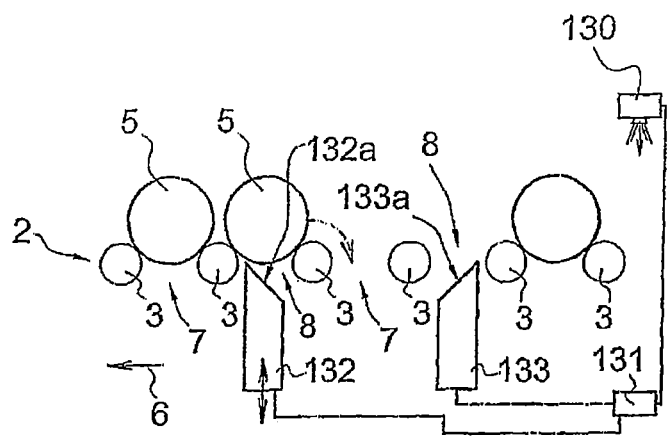
Figure 13B:
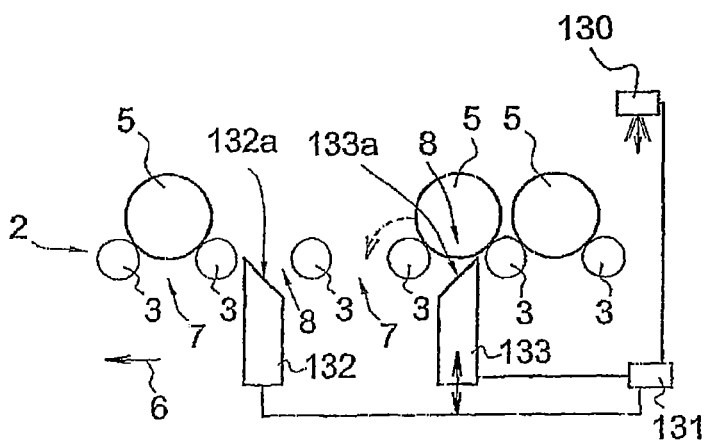
Figure 13C:
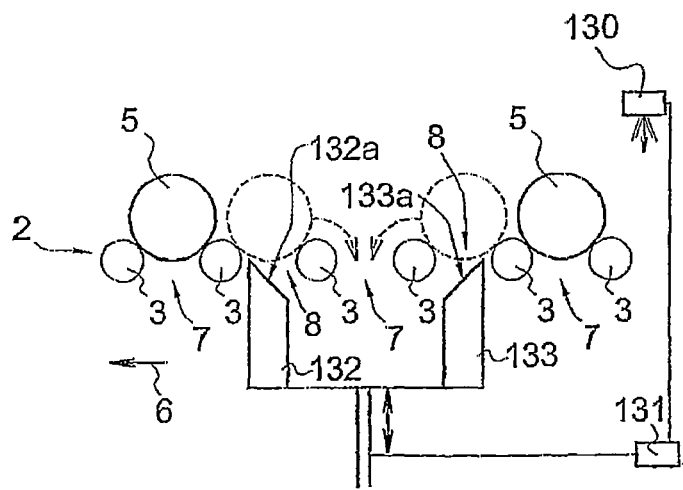

In the embodiment shown in FIG. 13 the device has two movement elements lying one behind the other in the direction of conveyance, which movement elements are in the form of ejection elements 132 and 133 respectively, which can move from the bottom in between two rollers 3 and in so doing can push upwards an egg 5 present in that space 8. The front ejection element 132, viewed in the direction of conveyance 6 of the conveyor 2, has a displacement surface 132a slanting backwards, by means of which an incorrectly lying egg 5 is flipped over the roller 3 behind it to the appropriate receiving space 7, as is illustrated in FIG. 13a. The rear ejection element 133, viewed in the direction of conveyance 6, has a displacement surface 133a slanting forwards, by means of which an incorrectly lying egg 5 is flipped over the roller 3 in front of it to the appropriate receiving space 7, as is illustrated in FIG. 13b. The ejection elements 132, 133 can be operated individually by means of the control unit 131. As an alternative, it is also conceivable for the ejection elements 132, 133 to be physically connected to each other, as is shown in FIG. 13c, and therefore to be operated simultaneously by the control unit 131. The ejection elements 132 and 133 respectively can also be placed above the rollers 3, in which case they move downwards when an egg is in the incorrect position.

The device according to FIG. 13 works as follows:

If the photoelectric cell 130 detects on the conveyor 2 a receiving space 7 with an egg 5 in it and then detects the presence of an egg 5 in the following space 8, as shown in FIG. 13a, the control unit 131 can establish that the latter egg 5 is one place forward. On the basis of that finding, the control unit 131 sends a control signal to the front ejection element 132 when the incorrectly filled space 8 is passing this ejection element 132 so that the egg 5 is flipped over the roller 3 to the receiving space 7 lying behind that space.

If the photoelectric cell 130 detects two empty spaces 8 and 7 respectively, as shown in FIG. 13b, the control unit 131 establishes that behind that point there is an egg 5 that is one place too far behind. On the basis of that finding, the control unit 131 sends a control signal to the rear ejection element 133 when the incorrectly filled space 8 is passing this ejection element 133 so that the egg 5 is flipped over the roller 3 to the receiving space 7 lying in front of that space.

The embodiment of FIG. 13c works in the same way as the embodiment of FIG. 13a and FIG. 13b, the only difference being that the two ejection elements 132 and 133 move simultaneously, with one of them therefore performing a dummy movement, i.e. it will not push an egg 5.

The embodiment shown in FIG. 14 has as its movement means a rotor 140 with radially extending pushing elements 141, which rotor 140 is fitted above the conveyor 2. The end area of each of the pushing elements 141 can act upon an egg 5 upon rotation of the rotor 140.

Figure 14A:
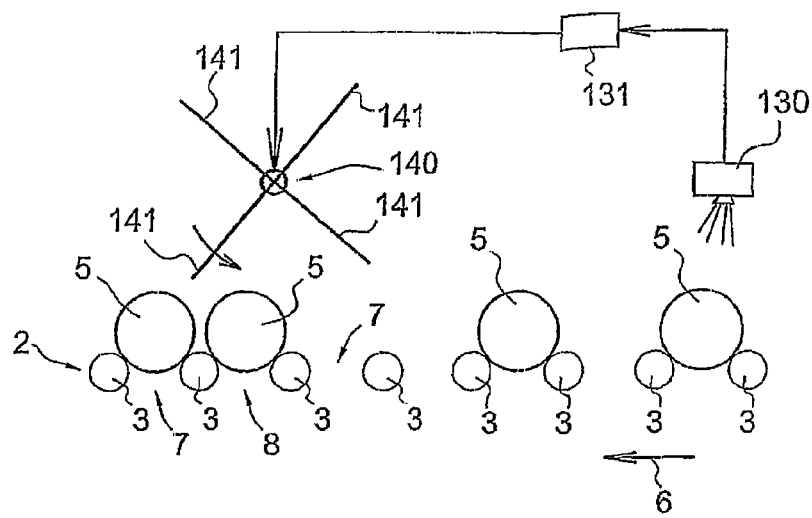
FIGS. 14a and 14b show a diagrammatic view of a part of another alternative embodiment of a conveying device according to a first aspect of the invention, provided with detection means and movement means.

If the photoelectric cell 130 detects a receiving space 7 on the conveyor 2 with an egg 5 in it and then detects the presence of an egg 5 in the following space 8, as shown in FIG. 14a, the control unit 131 can establish that the latter egg 5 is one place too far forward. On the basis of that finding, the control unit 131 sends a control signal to the rotor 140, which then begins to turn in such a way (anticlockwise in the figure) when the incorrectly placed egg 5 comes within the range of the rotor 140 that one of the pushing elements 141 pushes the incorrectly placed egg 5 backwards (i.e. against the direction of conveyance 6 of the conveyor 2) over the roller 3 behind, so that the egg 5 goes into the correct receiving space 7.

Figure 14B:
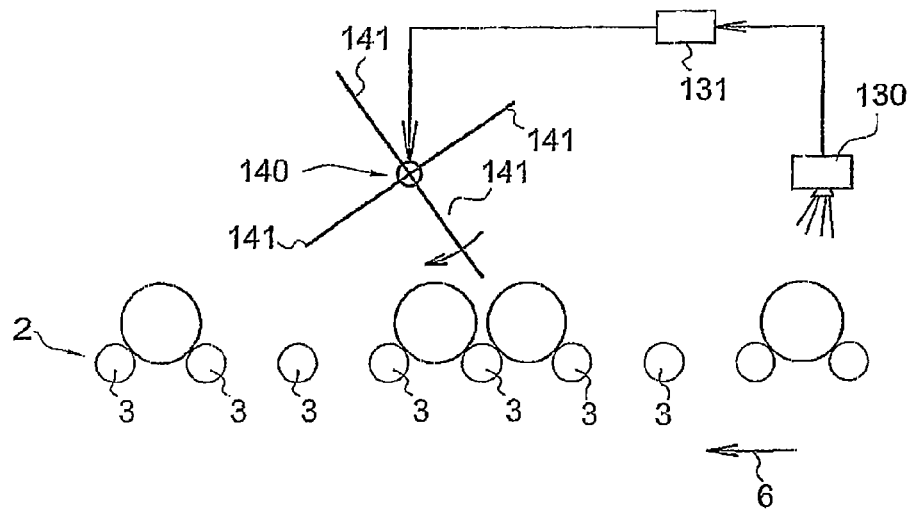

If the photoelectric cell 130 detects two empty spaces 8 and 7 respectively, as shown in FIG. 14b, the control unit 131 establishes that behind that point there is an egg 5 that is one place too far behind. On the basis of that finding, the control unit 131 sends a control signal to the rotor 140, which then begins to turn in such a way when the incorrectly placed egg 5 comes within the range of the rotor that one of the pushing elements 141 pushes the incorrectly placed egg 5 forwards (i.e. in the direction of conveyance 6 of the conveyor 2) over the roller 3 in front, so that the egg 5 goes into the correct receiving space 7.

The pushing elements 141 are preferably made of a flexible material. The rotor with the pushing elements could also be designed as a sort of brush.

As an alternative to the rotor 140, it is also conceivable to have a flap which is rotatable/movable with a certain stroke from left to right and vice versa. Furthermore, it is also possible to use a suction cup as a movement means, which suction cup is controlled by the control unit 131 to pick up an incorrectly placed egg and deposit it in the correct receiving space 7.

Figure 11:
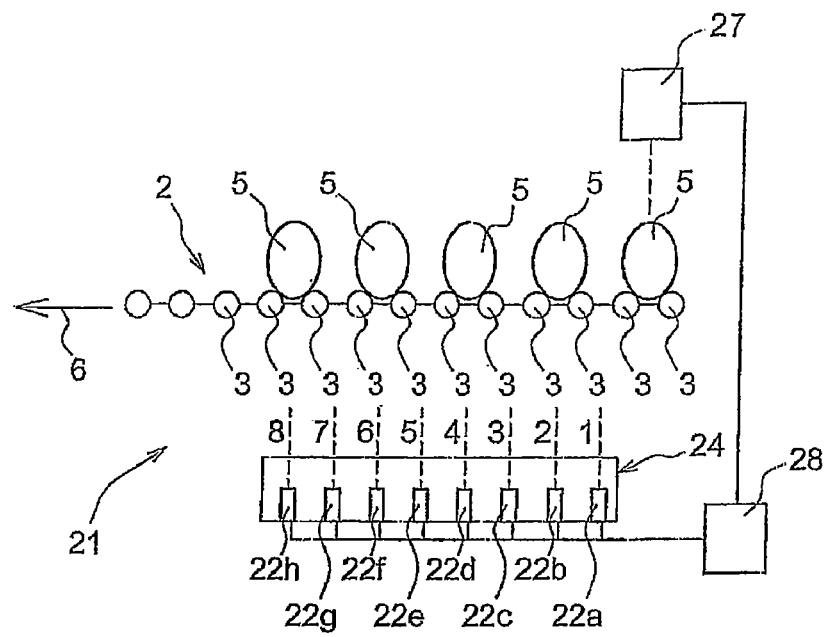
FIG. 11 shows a side view of a preferred embodiment of an inspection device according to a second aspect of the invention.
Figure 12:
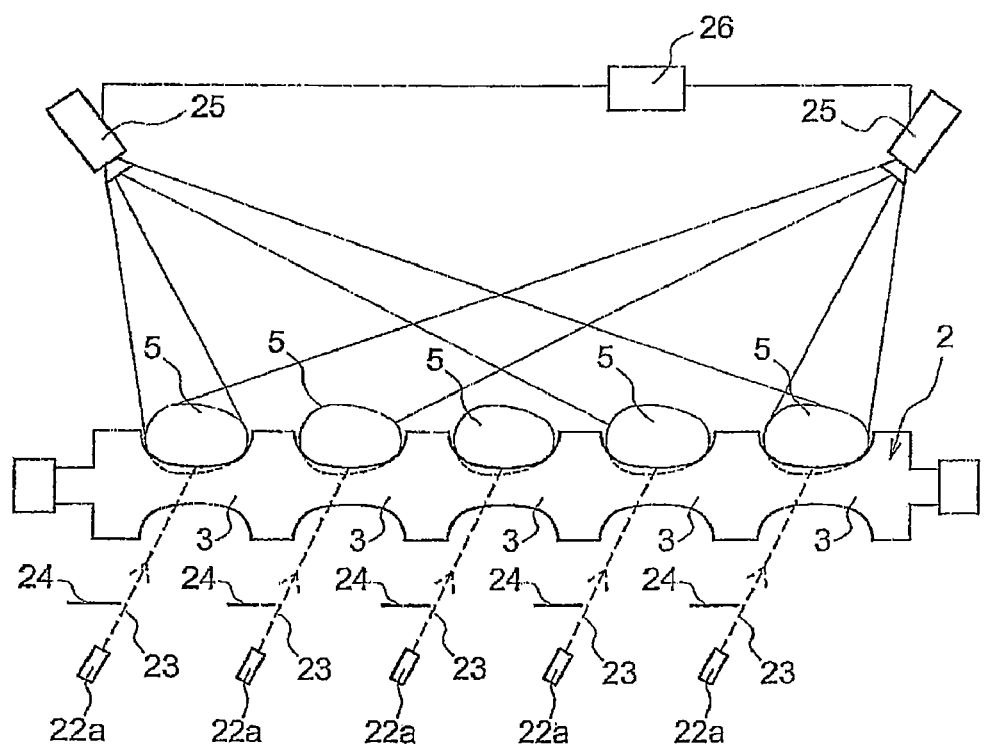
FIG. 12 shows a cross section of the inspection device of FIG. 11, FIGS. 13a-13c show a diagrammatic view of a part of an alternative embodiment of a conveying device according to a first aspect of the invention, provided with detection means and movement means.

FIG. 11 and FIG. 12 show diagrammatically an inspection device 21 for inspecting eggs 5 for cracks. The inspection device 21 comprises a conveying device 1 of the type described above with reference to FIGS. 1-10. The conveyor 2 comprises in general rows of a plurality of rollers, for example six, placed next to each other widthwise (see FIG. 12). Six eggs 5 can therefore be placed next to each other widthwise on the conveyor 2. The inspection device 21 has for each row of eggs a plurality of lasers 22a-22h, eight in the example shown, disposed in a stationary position one behind the other in the direction of conveyance 6. In the case of six eggs 5 per row forty-eight lasers are therefore provided. The lasers 22a-22h are placed in a slanting position below the conveyor belt of the egg 5 in order to expose the egg 5 to a laser beam 23 in a direction crosswise to the direction of conveyance 6, shown in FIG. 12. Since the lasers 22 are not placed directly below the conveyor belt of the egg 5, they will not become soiled so quickly because nothing will fall on them if, for example, an egg 5 is broken. If there is not sufficient space to place the lasers 22a-22h at the side of a conveyor belt of an egg 5, a shield plate 24 can be fitted as an alternative or as an addition, as can best be seen in FIG. 12.

The inspection device 21 furthermore comprises cameras 25 or the like for optical observation of the light transmission by the egg 5. The visual field of the cameras 25 always covers the full width of the conveyor 2, and eight rows of receiving spaces 7, so, because the rows according to the first aspect of the invention are filled alternately, four rows of eggs. The cameras 25 are placed opposite each other in the widthwise direction and view the eggs 5 at an angle from the top in the widthwise direction, each from a different side. Since the eggs 5 are set in rotation by the conveyor 2, the cameras 25 see the entire surface during the movement of the eggs 5.

The inspection device 21 furthermore comprises data processing means 26, for example image processing means for processing a locally observed increase in light transmission of the laser light through the shell surface of the egg 5 and converting it into a decision signal that is representative of the decision that the egg 5 contains a crack. An egg 5 with a crack can then be removed by means of ejection means (not shown) of the conveyor 2. The broken eggs are sorted out in this way.

The inspection device 21 furthermore comprises a photoelectric cell 27 or another, preferably contactless, detection means such as, for example, a capacitive limit switch, an ultrasonic switch or even a mechanical switch. The photoelectric cell 27, viewed in the direction of conveyance, is placed in front of the lasers 22a-22h, so that it detects whether an egg 5 is present in the receiving space 7 between two rollers 3 before the receiving spaces 7 start to move past the lasers 22a-22h. The photoelectric cell 27 is connected to a control unit 28 for the lasers 22a-22h. The control unit 28 is connected to the lasers 22a-22h and is equipped to switch on the lasers 22a-22h one after the other, depending on the detection signal emitted by the photoelectric cell 27, at the moment when the receiving space 7 containing an egg 5 passes the laser 22a-22h concerned, and to switch them off again when the receiving space 7 has passed the laser 22a-22h concerned. So, per detected egg 5 the front laser 22a is switched on first and is switched off when the egg 5 has passed, while the second laser 22b is switched on, and so on. In this way the eight lasers 22a-22h positioned one after the other in the direction of conveyance 6 are turned on and turned off again one after the other. This switching on and switching off of the lasers 22a-22h in each case is necessary in order to ensure that the laser beam 23 does not fall through openings in the conveyor 2 directly upon the cameras and blind said cameras. So if no egg 5 is detected in an receiving space 7, the lasers 22a-22h will not be switched on when that receiving space 7 is passing.

Figure 15:
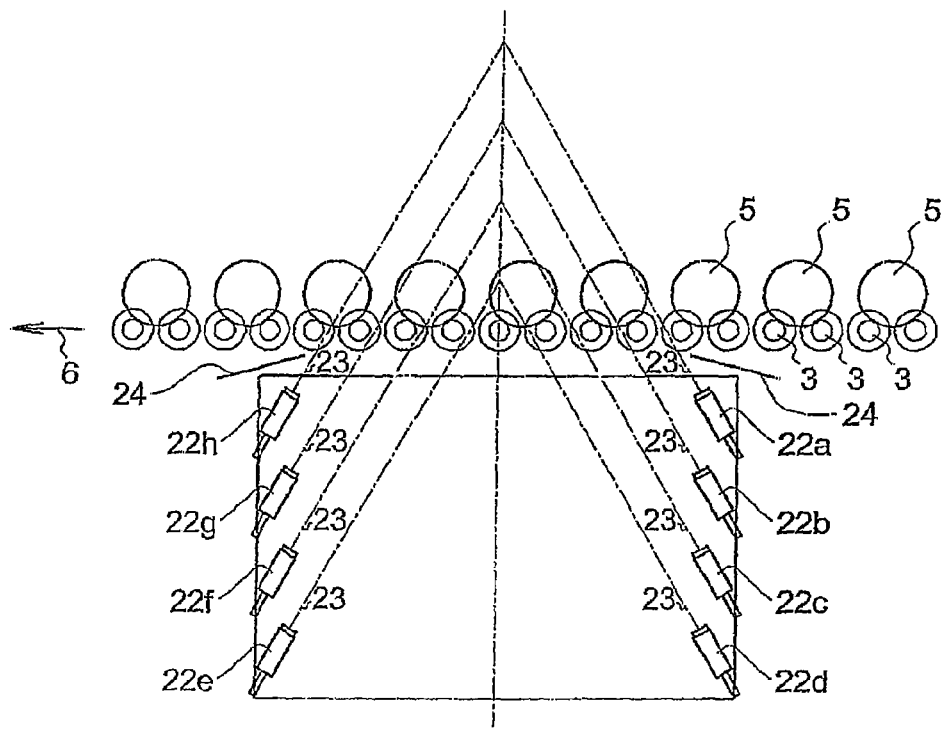
FIG. 15 shows a side view of another preferred embodiment of an inspection device according to a second aspect of the invention.

FIG. 15 shows an alternative laser arrangement. In this embodiment a set of four lasers 22a-22d and 22e-22h respectively is placed one below the other in each case. Each set of lasers 22a-22d and 22e-22h respectively is placed below a shield plate 24 in order to prevent soiling. The set of lasers 22a-22d shines upwards at an angle in the direction of conveyance 6 of the conveyor 2. The other set of lasers 22e-22h shines upwards against the direction of conveyance 6 of the conveyor 2. The lasers 22a-22h are placed relatively close to the conveyor, so that high standards do not need to be set for the alignment of the lasers 22a-22h. It is furthermore advantageous that below the plane where the cameras 25 view the eggs there is no need for lasers or other structural parts which through reflections could interfere with the detection of cracks. The cameras 25 are preferably situated in the plane perpendicular to the drawing, indicated by 150.

The lasers 22a-22h go on and off as in the case of the earlier embodiment. In the situation shown in FIG. 15 the lasers 22b, 22d, 22f and 22h are switched on, and the remaining lasers are switched off. On further movement of the conveyor 2 relative to the lasers, the lasers 22b, 22d, 22f and 22h will be switched off, and the remaining lasers switched on. In this way four eggs 5 in a row are exposed by four of the eight lasers 22a-22 in each case.

Although this is not preferable at the present time, in another embodiment (not shown) the lasers could all be placed on one side beside the conveyor 2. The advantage is that no soiling of the lasers can occur because they are situated beside the conveyor. The disadvantage is that the distance of the lasers from the eggs on the opposite side is relatively great, with the result that higher requirements are set for the alignment of the lasers.

What is claimed is:

1. A conveying device for conveying eggs, comprising: an endless conveyor provided with rollers extending transversely to the direction of conveyance, which rollers are placed at such a centre-to-centre distance from each other that they form between them a receiving space, in which in use an egg is received in such a way that the egg rests on both rollers, which rollers are rotatably mounted and can be driven so that in use they set an egg resting on them in rotation, and furthermore comprising a transfer device provided with a plurality of pick-up elements for picking up the eggs from a tray and placing the eggs on the conveyor, wherein the rollers are arranged in pairs and each receiving space is formed by a pair of rollers, and wherein the pick-up elements on the transfer device can be moved from a first position in which they are positioned at a distance from each other corresponding to the distance between the individual eggs on the tray, viewed in the direction of conveyance, and a second position corresponding to the centre-to-centre distance between two receiving spaces on the conveyor, viewed in the direction of conveyance, wherein blocking elements are provided, each positioned or capable of being positioned in a space between two pairs of rollers, in order to block incorrect positioning of eggs in that space, wherein the blocking elements are provided on an endless circulating means, which in operation runs at the same speed as the conveyor, the blocking elements extending from the circulating means and in operation being insertable into a space between two pairs of rollers, wherein the endless circulating element with the blocking elements is fitted below the conveyor so that the blocking elements can be inserted into the space between the pairs of rollers from the underside of the conveyor, and wherein a plurality of blocking elements are fitted one after the other on a frame, and wherein the circulating means comprises a paternoster system for conveying the frames around in a fixed orientation.

2. The device according to claim 1, wherein viewed in the direction of conveyance, the rear roller of a pair of rollers and a front roller of a pair of rollers situated directly behind are connected to each other by means of a connecting element, and a blocking element extending into the space between said rollers is provided on the connecting element.

3. The device according to claim 1, wherein the blocking elements comprise pins or lips extending substantially perpendicularly to the circulating means.

4. The device according to claim 1, wherein the endless circulating means is in the form of a chain.

5. An inspection device for inspecting eggs for cracks, comprising;

a conveying device for conveying the eggs in a conveying direction, the conveying device having one or more rows, each row extending in the conveying direction, and the conveying device furthermore being adapted to rotate the eggs during the conveyance, associated with each one of said rows of the conveyor, a plurality of lasers disposed in a stationary position one after the other in the direction of conveyance, for the purpose of exposing an egg of said row successively to each stationary laser beam of the successive lasers of the said plurality of lasers during the movement of the egg by means of the conveying device, optical observation means for observing a light transmission by the eggs resulting from the exposure to said laser beam, and data processing means that on the basis of the light transmission observed by the observation means are adapted to emit a decision signal that is representative for the decision of whether or not an egg has a crack.

6. The inspection device according to claim 5, wherein the lasers are placed in a slanting position below the conveyor belt of the egg in order to expose the egg to a laser beam in a direction crosswise to the direction of conveyance.

7. The inspection device according to claim 5, wherein the device comprises detection means for detecting whether an egg is present in the receiving space between two rollers, which detection means are connected to a control unit for the lasers, which control unit is equipped to switch on the lasers in succession, depending on the egg detection by the detection means, at the moment when the receiving space containing an egg is passing the particular laser and to switch them off again when the receiving space has passed the laser concerned.

8. The inspection device according to claim 5, wherein the conveying device comprises a conveying device for conveying eggs, comprising an endless conveyor provided with rollers extending transversely to the direction of conveyance, which rollers are placed at such a centre-to-centre distance from each other that they form between them a receiving space, in which in use an egg is received in such a way that the egg rests on both rollers, which rollers are rotatably mounted and can be driven so that in use they set an egg resting on them in rotation, and furthermore comprising a transfer device provided with a plurality of pick-up elements for picking up the eggs from a tray and placing the eggs on the conveyor, wherein the rollers are arranged in pairs and each receiving space is formed by a pair of rollers, and wherein the pick-up elements on the transfer device can be moved from a first position in which they are positioned at a distance from each other corresponding to the distance between the individual eggs on the tray, viewed in the direction of conveyance, and a second position corresponding to the centre-to-centre distance between two receiving spaces on the conveyor, viewed in the direction of conveyance.

9. The inspection device according to claim 5, wherein a shield plate is fitted above the lasers.

10. The inspection device for inspecting eggs for cracks, comprising:
   a conveying device for conveying the eggs in a conveying direction, the conveying device having one or more rows, each row extending in the conveying direction, and the conveying device furthermore being adapted to rotate the eggs during the conveyance,
   associated with each one of said rows of the conveyor, a plurality of lasers which are arranged in sets, wherein in each set a plurality of lasers is disposed in a stationary position one below the other, wherein the lasers of the set are directed upward at an angle such that the laser beam aims in the direction of conveyance or against the direction of conveyance for the purpose of exposing an egg of said row successively to each stationary laser beam of the successive lasers of the set during the movement of the egg by means of the conveying device, the sets of lasers being disposed in a stationary position one after the other in the direction of conveyance, such that an egg of said row is exposed successively by the laser beams of the successive sets,
   optical observation means for observing a light transmission by the eggs resulting from the exposure to said laser beam,
   data processing means that on the basis of the light transmission observed by the observation means are adapted to emit a decision signal that is representative for the decision of whether or not an egg has a crack, 11. The inspection device according to claim 10, wherein the lasers are disposed substantially directly below the conveyor belt of the egg for the purpose of exposing the egg to a laser beam in the direction of conveyance or against the direction of conveyance.

12. The inspection device according to claim 5, wherein the observation means comprise at least one camera which observes the egg during its movement past the lasers disposed one after the other.

13. The inspection device according to claim 12, wherein two cameras are provided on either side at an angle above the conveyor belt of the egg, which cameras are directed in such a way that the entire upper surface of the egg can be observed.

14. The inspection device according to claim 10, wherein the observation means comprise at least one camera which observes the egg during its movement past the lasers disposed one after the other.

15. The inspection device according to claim 14, wherein two cameras are provided on either side at an angle above the conveyor belt of the egg, which cameras are directed in such a way that the entire upper surface of the egg can be observed.

16. The inspection device according to claim 10, wherein the conveying device comprises a conveying device for conveying eggs, comprising an endless conveyor provided with rollers extending transversely to the direction of conveyance, which rollers are placed at such a centre-to-centre distance from each other that they form between them a receiving space, in which in use an egg is received in such a way that the egg rests on both rollers, which rollers are rotatably mounted and can be driven so that in use they set an egg resting on them in rotation, and furthermore comprising a transfer device provided with a plurality of pick-up elements for picking up the eggs from a tray and placing the eggs on the conveyor, wherein the rollers are arranged in pairs and each receiving space is formed by a pair of rollers, and wherein the pick-up elements on the transfer device can be moved from a first position in which they are positioned at a distance from each other corresponding to the distance between the individual eggs on the tray, viewed in the direction of conveyance, and a second position corresponding to the centre-to-centre distance between two receiving spaces on the conveyor, viewed in the direction of conveyance.

17. The inspection device according to claim 10, wherein a shield plate is fitted above the lasers.

18. A conveying device for conveying eggs, comprising an endless conveyor provided with rollers extending transversely to the direction of conveyance, which rollers are placed at such a centre-to-centre distance from each other that they form between them a receiving space, in which in use an egg is received in such a way that the egg rests on both rollers, which rollers are rotatably mounted and can be driven so that in use they set an egg resting on them in rotation, and furthermore comprising a transfer device provided with a plurality of pick-up elements for picking up the eggs from a tray and placing the eggs on the conveyor, wherein the rollers are arranged in pairs and each receiving space is formed by a pair of rollers, and wherein the pick-up elements on the transfer device can be moved from a first position in which they are positioned at a distance from each other corresponding to the distance between the individual eggs on the tray, viewed in the direction of conveyance, and a second position corresponding to the centre-to-centre distance between two receiving spaces on the conveyor, viewed in the direction of conveyance,
   wherein a paternoster system is fitted below the conveyor, said paternoster system comprising an endless circulating means which in operation runs at the same speed as the conveyor and furthermore comprising frames on which a plurality of blocking elements are fitted one after the other, which paternoster system conveys the frames around in a horizontal orientation, wherein the blocking elements are insertable from underside of the conveyor into the spaces between the pairs of rollers, in order to block incorrect positioning of eggs in that space.

* * * * *